(12) United States Patent
Ling et al.

(10) Patent No.: US 9,345,797 B2
(45) Date of Patent: May 24, 2016

(54) GRAPHENE-BASED ANTIBACTERIAL THERAPY AND USING THE SAME

(71) Applicant: NATIONAL TSING HUA UNIVERSITY, Hsinchu (TW)

(72) Inventors: Yong-Chien Ling, Hsinchu (TW); Archana Ramchandra-Deokar, Hsinchu (TW); Meng-Chin Wu, Taipei (TW); Chan-Hung Liao, Tainan (TW); Po-Yuan Shih, Taipei (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 150 days.

(21) Appl. No.: 14/019,273

(22) Filed: Sep. 5, 2013

(65) Prior Publication Data

US 2015/0004055 A1 Jan. 1, 2015

(30) Foreign Application Priority Data

Jun. 28, 2013 (TW) .............................. 102123168 A (51) Int. Cl.
*A61L 2/08* (2006.01)
*C07F 15/02* (2006.01)
*A01N 35/10* (2006.01)

(52) U.S. Cl.
CPC ................. *A61L 2/088* (2013.01); *A01N 35/10* (2013.01); *C07F 15/02* (2013.01)

(58) Field of Classification Search
CPC ......... A61L 2/088; B01D 69/12; C07F 15/02; A01N 35/10; A01N 25/10
See application file for complete search history.

(56) References Cited

U.S. PATENT DOCUMENTS

| 8,468,611 | B2* | 6/2013 | Riedo et al. ...................... 850/33 |
| 2011/0014492 | A1* | 1/2011 | Joshi et al. .................... 428/626 |
| 2012/0220053 | A1* | 8/2012 | Lee et al. ....................... 436/501 |
| 2013/0105400 | A1* | 5/2013 | Lee et al. ....................... 210/688 |
| 2013/0123514 | A1* | 5/2013 | Bielawski et al. .............. 549/72 |
| 2013/0202945 | A1* | 8/2013 | Zhamu et al. ................. 429/156 |
| 2013/0210115 | A1* | 8/2013 | Kim et al. ..................... 435/188 |
| 2014/0001123 | A1* | 1/2014 | Kaledin et al. ................ 210/660 |
| 2014/0011972 | A1* | 1/2014 | Bielawski et al. ............ 526/204 |
| 2014/0134092 | A1* | 5/2014 | Shankman ................. 423/415.1 |

FOREIGN PATENT DOCUMENTS

CN 102590506 A * 7/2012 ........... G01N 33/569

OTHER PUBLICATIONS

English translation of CN 102590506 A, Jul. 2012.*

* cited by examiner

*Primary Examiner* — Regina M Yoo
(74) *Attorney, Agent, or Firm* — Muncy, Geissler, Olds & Lowe, P.C.

(57) ABSTRACT

Photothermal antibacterial material RMG is provided in the present invention, where R represents aldehyde, di-aldehyde or multi-aldehyde, M is magnetic material, and G is reduced graphene oxide. A method of synthesizing the abovementioned antibacterial material comprises of three steps. At first graphene oxide was synthesized, followed by simultaneous reduction and functionlization with MNPs and eventually an aldehyde is modified on magnetic material to yield magnetic G functionalized glutaraldehyde (RMG). We utilize the photothermal feature of graphene for antibacterial activity, in addition graphene was functionalized with aldehyde for capturing bacteria and with magnetic material to enhance a focusing of light irradiation. Moreover, the magnetic properties of material could help for reusability of antibacterial material.

2 Claims, 9 Drawing Sheets

|  | Survival rate (%) | | | |
|---|---|---|---|---|
|  | Dark | | NIR illumination | |
| Material \ Bacteria | S. aureus | E. Coli | S. aureus | E. Coli |
| N/A | - | - | 155% ± 15 | 102% ± 14 |
| Magnetic G | 143% ± 50 | 117% ± 34 | 45% ± 14 | 39% ± 12 |
| G with the modification of glutaraldehyde | 147% ± 20 | 108% ± 15 | 0.4% ± 0.1 | 0.1% ± 0.1 |

FIG. 8

GRAPHENE-BASED ANTIBACTERIAL THERAPY AND USING THE SAME

CROSS-REFERENCE TO RELATED APPLICATIONS

This Non-provisional application claims priority under 35 U.S.C. §119(a) on Patent Application No(s). 102123168 filed in Taiwan, Republic of China, Jun. 28, 2013, the entire contents of which are hereby incorporated by reference.

FIELD OF THE INVENTION

This present invention relates to graphene-based antibacterial derivatives, especially method of synthesizing and using them by utilizing reduced graphene oxide (RGO) modified with magnetic nanoparticles (MNPs) and aldehydes.

BACKGROUND OF THE INVENTION

Microorganisms can be classified into coccus, *bacillus*, trichobacteria or *spirillum* according to their shapes which comprises of protists larger than bacteria, or virus smaller than bacteria. The microorganisms are pretty important for body circulation, digestion and metabolism, manufacture of foods and industrial goods such as wine, soya sauce or vinegar alcohol, butyl alcohol, propyl alcohol, lactate or citric acid for preventing environmental pollution. However, most of twenty hundred thousand kinds of the microorganisms are harmful to human mankind, causes diseases, such as pulmonary tuberculosis, gonorrhea, plague or sand holes It become crucial to find a method of wiping the microorganism to prevent and treat these infections.

Potential antibacterial derivatives have better opportunities in a market that fits the changing need of the society. In early twenty's they were applied for daily necessities and electrical appliances. Further, they were expansively and quickly utilized to the architectures, decorations, plastic or rubbers, coatings, resin, food packaging materials and fibers. Even the requests of the high technology or the high additional value products, such as medical equipment's used in the hospital, indeed need potential antibacterial derivatives.

Recently, several antibacterial methods are disclosed, such as UV disinfection lamp and photocatalysts. The former utilizes the high absorption of the nucleic acid and protein with respect to their absorption wavelength 254 nm to destroy nucleic acid, DNA or RNA within bacteria. The latter is performed by utilizing the production of electron/hole pairs, and followed by reaction of ambient air/moisture with photocatalyst to form radicals, when microorganisms come in contact with these radicals they degraded into smaller molecules.

However, the apparatus of the UV disinfection lamp is too huge, hence not portable. On the other hand, UV light will produce $O_3$, which is harmful to human's health. As to the radicals produced from the photocatalyst, their cytotoxicity remains a big issue and eventually cannot be directly applied onto the medical equipment's.

SUMMARY OF THE INVENTION

According to the aforementioned disadvantages of the prior art, the present invention provides a graphene-based antibacterial material to absorb light irradiation (NIR, 808 nm, 1.5 W/cm$^2$) and release as a heat to kill the captured bacteria. In present invention, antibacterial material is represented by RMG, wherein R represents aldehyde, di-aldehyde or multi-aldehyde, M is a magnetic material, and G is reduced graphene oxide.

Preferably, R is formaldehyde, straight chain C1-10 alkyl, branched C3-10 alkyl, C3-10 cycloalkyl, phenyl or phenylalkyl aldehyde.

Preferably, R is straight chain alkyl di-aldehyde, branched alkyl di-aldehyde, aromatic di-aldehyde, alkylaromatic di-aldehyde, heteroaromatic di-aldehyde, alkyl heteroaromatic di-aldehyde or their mixture. Preferably, R is glutaraldehyde.

Preferably, R is straight chain alkyl multi-aldehyde, branched alkyl multi-aldehyde, aromatic multi-aldehyde, alkylaromatic multi-aldehyde, heteroaromatic multi-aldehyde, alkyl heteroaromatic multi-aldehyde or their mixture.

Preferably, magnetic material is $Fe_3O_4$ nanoparticles and synthesized with a size distribution from ~5 to 8 nm.

Preferably, the bacteria are gram-positive or gram-negative bacteria.

Preferably, the light source is a near-infrared (NIR) light source.

The present invention further provides a method of synthesizing an antibacterial material to absorb light irradiation and release as a heat to kill the captured bacteria. The method comprises of the following steps: at first, graphene oxide (GO) was synthesized, followed by its simultaneous reduction and functionalization with MNPs An aldehyde is then modified onto the surface of the magnetic material as bacteria capturing agent.

Preferably, the step of synthesizing the graphene oxide is performed by utilizing a modified Hummer's method.

Preferably, the step of performing simultaneous reduction and functionalization with a magnetic material further comprises of following steps: first, an iron-containing solution and a suspension containing the graphene oxide are provided for the formation of MNPs onto GO nanosheets.

Preferably, the iron-containing solution is a solution containing ferric chloride, ferrous chloride or their mixture. Preferably, the step of providing the iron-containing solution further comprises of following steps: first, the ferric chloride and the ferrous chloride are mixed with a ratio of 2:1. The mixed ferric chloride and ferrous chloride are dissolved into distilled (DI) water to form the iron-containing solution.

Preferably, the step of producing the magnetic material is performed by rapid addition of ammonium hydroxide.

Preferably, the step of reducing GO further comprises of the following steps: adding hydrazine as a reducing agent.

Preferably, the aldehyde is glutaraldehyde.

The antibacterial material is represented by RMG wherein R represents aldehyde, di-aldehyde or multi-aldehyde, M is a magnetic material, and G is reduced graphene oxide. The present invention further provides a method of using an antibacterial material RMG. RMG was allowed to capture gram-positive or gram-negative bacteria, followed by irradiation with light source. Preferably, the light source is a NIR light source with a wavelength of 800 nm.

Preferably, the method disclosed in the present invention further comprising of following step: utilizing a magnet to attract the antibacterial material.

Preferably, M is $Fe_3O_4$ nanoparticles, and R is glutaraldehyde.

Preferably, the bacteria are gram-positive or gram-negative bacteria. Preferably, the gram-positive bacteria is *Staphylococcus aureus* (*S. aureus*). Preferably, the gram-negative bacteria is *Escherichia coli* (*E. coli*).

The features and advantages of the present invention will be understood and illustrated in the following specification and through FIG. 1-7B.

DETAILED DESCRIPTION OF THE INVENTION

According to the aforementioned disadvantages of the prior art, in the present invention efforts were taken to design an antibacterial material; which not only has low cytotoxicity but also its reproducibility could find the application in biomedical, health care or environmental cleaning. The antibacterial material is represented by a formula I:

RMG      I

Figure 1:
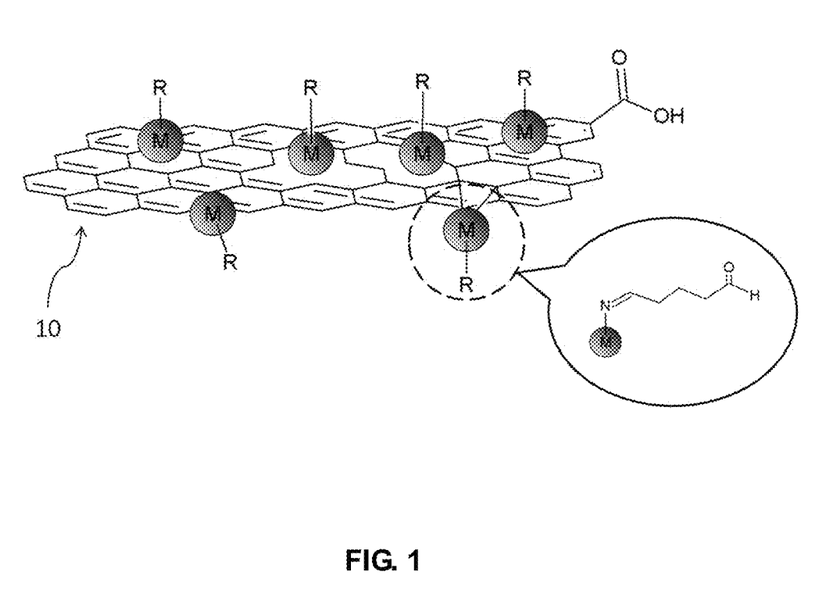
FIG. 1 represents the schematic for the antibacterial material according to an embodiment of the present invention.

As shown in the formula I, R represents aldehyde, di-aldehyde or multi-aldehyde, M is a magnetic material, and G is reduced graphene oxide. As shown in FIG. 1, the antibacterial material provided in the present invention utilized the reduced GO 10 as a substrate. The magnetic material M and aldehyde R are then modified on the reduced GO 10. The antibacterial material can capture the bacteria via the aldehyde R and further aggregated by utilizing the magnetic properties of material M. Aggregated antibacterial material along with captured bacteria is then irradiated with a light source to utilize the photothermal properties of reduced GO to emit heat for high-temperature sterilization of bacteria. Moreover, the magnetic properties of material could help for reusability of antibacterial material.

In a preferred embodiment, the aldehyde is represented by a formula II:

$R^1$—CHO      II

Where R is aldehyde, $R^1$ can be formaldehyde, straight chain C1-10 alkyl, branched C3-10 alkyl, C3-10 cycloalkyl, phenyl or phenylalkyl aldehyde. In another preferred embodiment, R is di-aldehyde and can be straight chain alkyl di-aldehyde, branched alkyl di-aldehyde, aromatic di-aldehyde, alkyl aromatic di-aldehyde, heteroaromatic di-aldehyde, alkyl heteroaromatic di-aldehyde or their mixture. Preferably, R is glutaraldehyde. However, the present invention is not limited thereto. That is, R can be straight chain alkyl multi-aldehyde, branched alkyl multi-aldehyde, aromatic multi-aldehyde, alkyl aromatic multi-aldehyde, heteroaromatic multi-aldehyde, alkyl heteroaromatic multi-aldehyde or their mixture. However, R is preferably glutaraldehyde.

Preferably, the magnetic material M can be iron (II, III) oxide nanoparticles ($Fe_3O_4$ nanoparticles) with a size distribution from ~5 to 8 nm. However, the present invention is not limited thereto.

Figure 2:
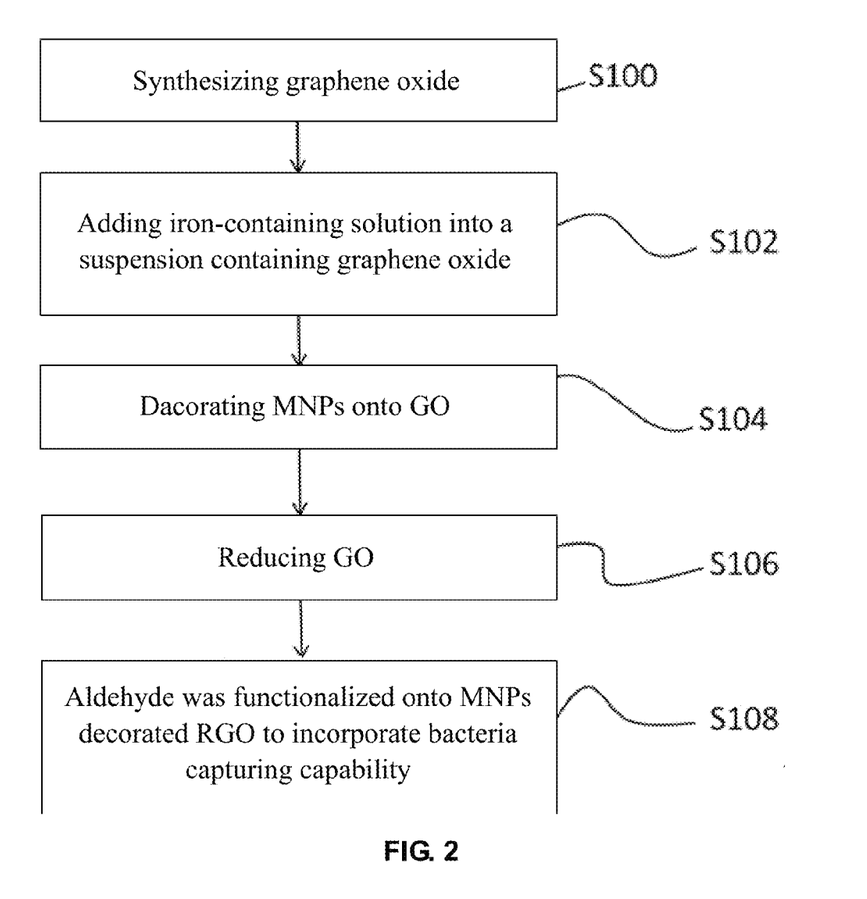
FIG. 2 represents a flow chart for synthesizing the antibacterial material according to the embodiment of the present invention.

FIG. 2 represents a flow chart for a method of synthesizing the antibacterial material RMG. As the first step towards the preparation of RMG, GO was synthesized as shown in step S100. In the preferred embodiment, the step S100 was synthesized by utilizing a modified Hummer's method. At first, graphite flakes were allowed to react with concentrated sulfuric acid, potassium permanganate and sodium nitrate, followed by addition of hydrogen peroxide therein for the removal of unreacted metal ions to achieve pure GO nanosheets.

A stable suspension of GO was prepared by exfoliating GO (0.35 g) in DI water. Iron (III) chloride hexahydrate ($FeCl_3.6H_2O$, 0.35 g) and iron (II) chloride tetrahydrate ($FeCl_2.4H_2O$, 0.2 g) with a ratio of 2:1 was dissolved in DI water (50 mL) to provide an iron-containing solution. As shown in the FIG. 2 (step S102), the iron-containing solution is added slowly into the suspension. Rapid addition of ammonia solution (0.5 mL) to the abovementioned solution and stirring for 1 h at 60° C. yielded MNPs as shown in step S104. Preferably, the MNPs are $Fe_3O_4$ nanoparticles.

The GO decorated was reduced in step S106, and then the MNPs were modified onto G. Preferably, hydrazine was used as a reducing agent in step S106. Moreover, the step S106 was preferably performed by adding 500 μL of hydrazine therein and reacting for 4 h at 90° C. However, the present invention is not limited thereto. $Fe_3O_4$ nanoparticles with the amino group modified thereon were finally modified on the G.

As shown in step S108 and FIG. 1, G with the magnetic material modified thereon was added into a solution containing aldehyde and stirred at RT for 24 h to let the aldehyde modify on the surface of the magnetic material via C═N bonding. Preferably, the solution containing the aldehyde is a solution containing 0.25% aldehyde, and the aldehyde is glutaraldehyde. However, the present invention is not limited thereto.

Figure 3A:
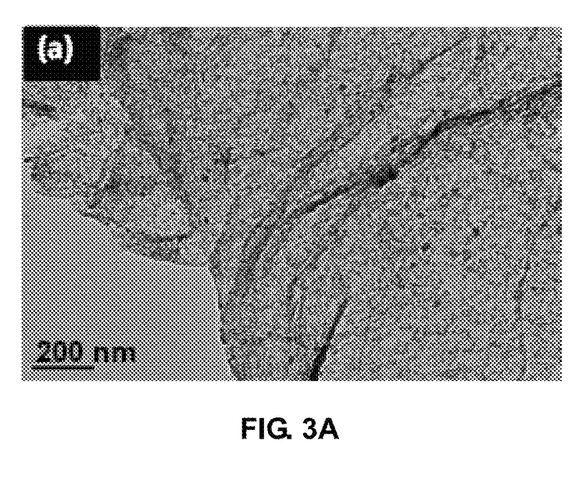
FIG. 3A and FIG. 3B represents transmission electron microscopic (TEM) and High-resolution TEM (HRTEM) images of the magnetic graphene based antibacterial material according to the preferred embodiment of present invention respectively.
Figure 3B:
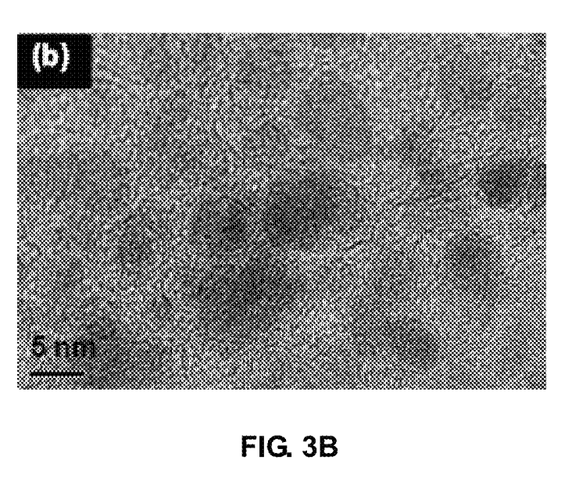
Figure 4:
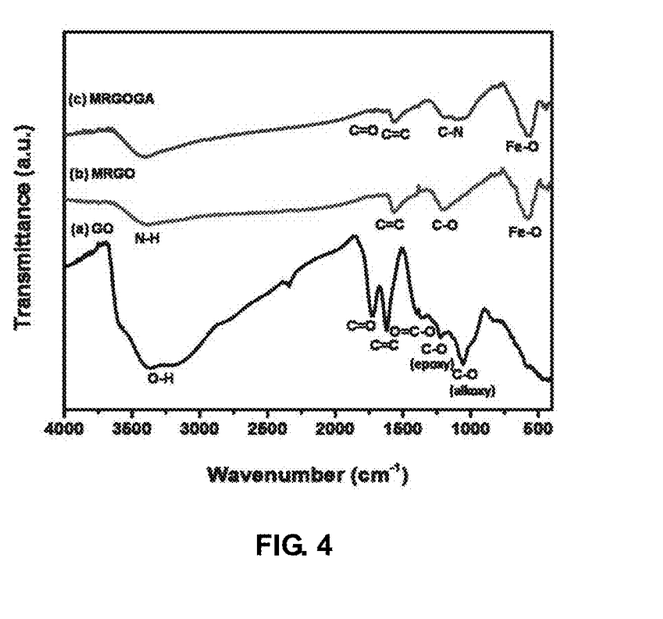
FIG. 4 represents the fourier transform-infrared (FT-IR) spectrum of the antimicrobial material MRGOGA.

FIG. 3A, FIG. 3B represents TEM and HRTEM images of the antibacterial material MG according to a preferred embodiment of the present invention respectively. Morphology of the antibacterial material was observed through TEM as shown in FIG. 3A, and $Fe_3O_4$ nanoparticles were uniformly decorated onto the G, with a size distribution within nanoscale. Preferably, FIG. 3B i.e. HRTEM image of MG demonstrates spherical MNPs with a size distribution from ~5 to 8 nm. The FIG. 4 shows a FT-IR spectrum of the preferred embodiment of the antibacterial material. Furthermore the FIG. 4 represents the FT-IR spectrum of the antimicrobial material MRGOGA.

Figure 5:
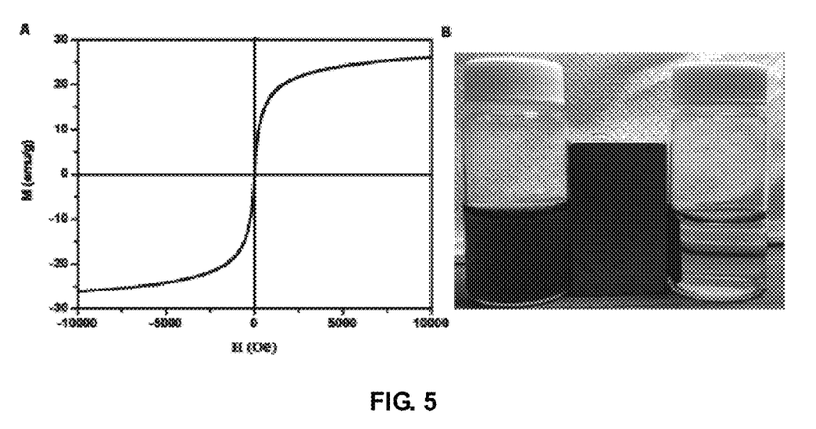
FIG. 5 represents a hysteresis curve of RMG by superconducting quantum interference device (SQUID) according to the embodiment of the present invention.

The magnetic properties of RMG were investigated using SQUID (FIG. 5A according to the embodiment of the present invention. RMG exhibits good superparamagnetic property with saturation magnetization value (Ms) ~26 emu $g^{-1}$ at 298 K, very low coercivity (He) ~8 $O_e$, and remanent magnetization ($M_r$) ~0.56 emu. $g^{-1}$. FIG. 5B presents the photograph of two vials filled with solution with a magnet attached to their outside. The solution in the left vial contains well dispersed GO and retains its brown color. On contrast, the solution in the right vial contains RMG and becomes colorless.

Figure 6A:
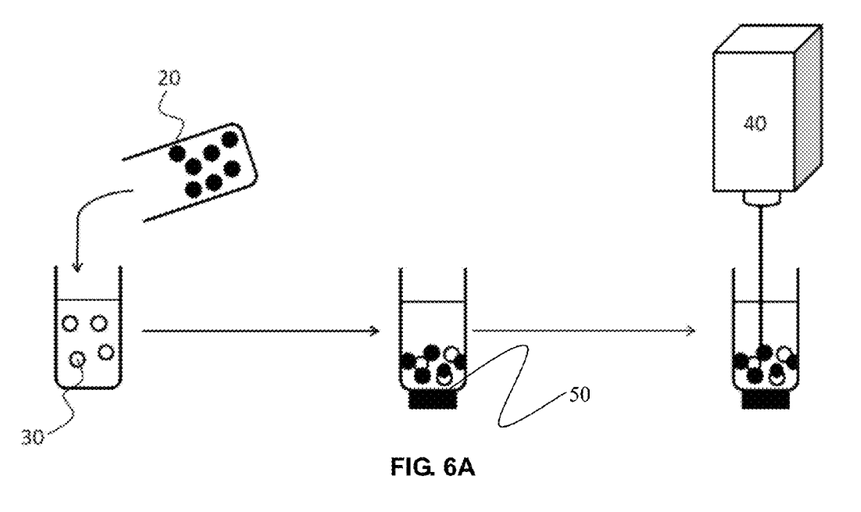
FIG. 6A represents a flow chart for utilization the antibacterial material according to the embodiment of present invention.
Figure 6B:
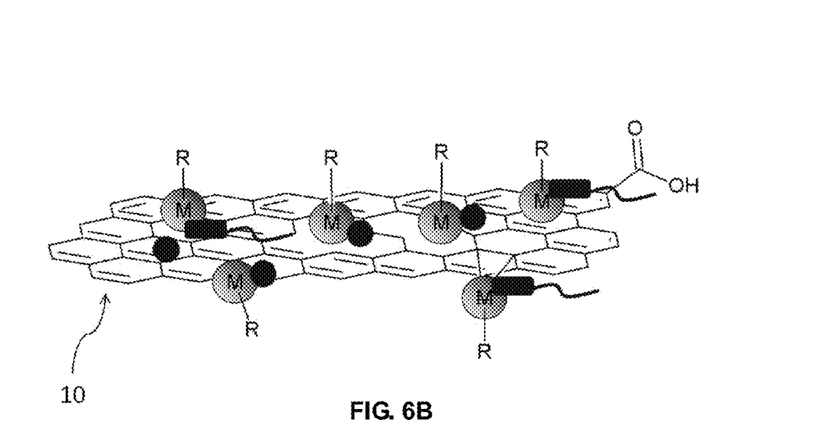
FIG. 6B represents a schematic demonstrating the bacteria captured by RMG.
Figure 6C:
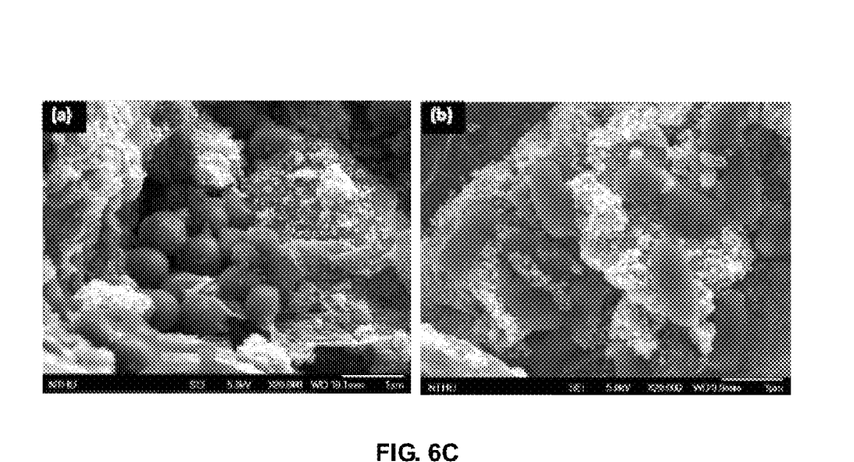
FIG. 6C represents scanning electron microscopic (SEM) images of RMG captured *E. coli* and *S. aureus* bacteria according to schematic FIG. 5B.

FIG. 6A is a flow chart demonstrating the method of using the antibacterial material RMG. At first, RMG (20) was dispersed in phosphate buffer solution (PBS) and allowed to interact with the bacterial strains (30, FIG. 6A) by vortexing, further the RMG captured bacteria were aggregated by applying an external magnet (50, FIG. 6A). Eventually mixture was subjected to NIR irradiation (40, FIG. 6A) to kill the bacteria. As mentioned before, the antibacterial material 20 provided in the present invention consists of the G, the magnetic material M and the aldehyde R. Therefore, the antibacterial material will capture the bacteria by utilizing cross-linking ability of R with the surface proteins of the bacteria (FIG. 6B). Preferably, the bacteria are gram-positive and gram-negative bacterial strains. Preferably, the gram-positive bacteria is *S. aureus*. Preferably, the gram-negative bacteria is *E. coli*. The SEM image (FIG. 6C) demonstrates that the antibacterial material RMG provided in the present invention can capture aforementioned two bacterial strains indeed.

The mixture containing the bacteria 30 and the antibacterial material 20 is modified with the magnetic material, such as $Fe_3O_4$ nanoparticles, therefore can be aggregated by applying an external magnet 50 to enhance the light irradiation effect. The G can effectively convert the light energy into heat for further high-temperature sterilization. Preferably, the light source 40 is NIR with a wavelength of 800 nm and an irradiation time is 10 min. However, the present invention is not limited thereto. After irradiating, the antibacterial material modified with the magnetic material, such as $Fe_3O_4$ nanoparticles, thereon can be aggregated for reproducibility by utilizing a magnet 50.

Figure 7A:
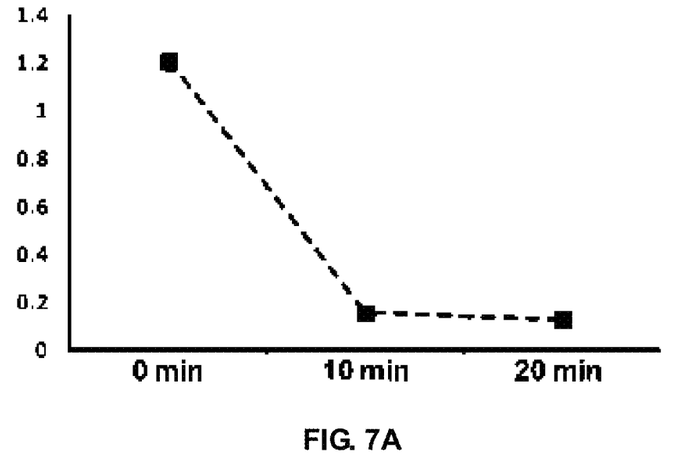
FIG. 7A and FIG. 7B represents the bacteria capturing capabilities of RMG for gram-positive and gram-negative bacteria respectively.
Figure 7B:
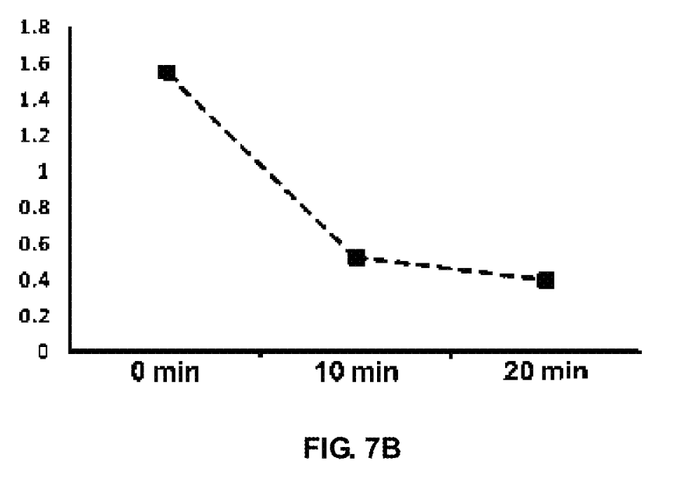

FIGS. 7A and 7B represents the bacteria capturing capabilities of the antibacterial material RMG by measuring $OD_{600nm}$ of *S. aureus* and *E. coli* respectively. It is noted that optical density at 600 nm ($OD_{600nm}$) indicates the density of bacteria in a medium. As shown in FIG. 7A and FIG. 7B, the $O.D_{600nm}$ for *S. aureus* decreased from 1.203 to 0.125 and for *E. coil* 1.541 to 0.396 upon interaction with the antibacterial material demonstrating bacteria capturing capability of RMG.

Figure 8:
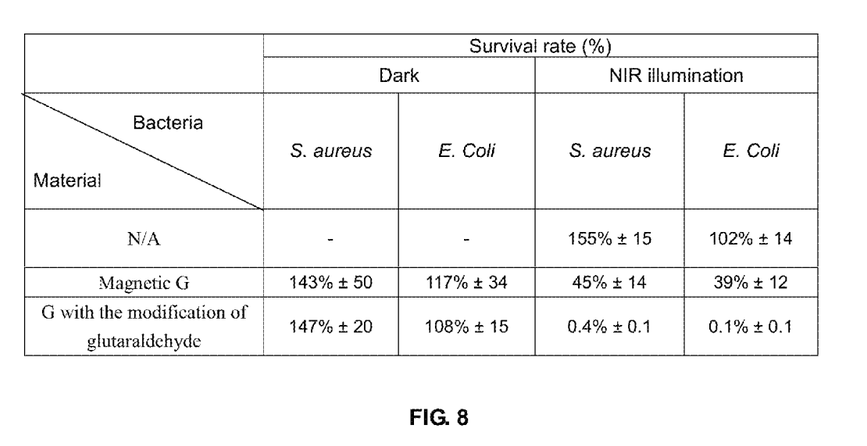
FIG. 8 represents the survival rate of *S. aureus* and *E. coli* (~$10^6$-$10^7$ CFU/mL) upon the interaction with antibacterial material RMG (80 ppm) for 10 min in dark and under NIR illumination.

FIG. 8 represents the survival rate of *S. aureus* and *E. coli* bacteria (~$10^6$-$10^7$ CFU/mL) for 80 ppm antibacterial material RMG solution under dark and NIR light for 10 min. Concentration of the bacteria after the treatment with antibacterial material modified glutaraldehyde (RMG) is lower than that of antibacterial material without the modification of the glutaraldehyde (RM). Antibacterial material modified with glutaraldehyde can dramatically reduced the concentration of the bacteria from one thousandth to four thousandth of the original (FIG. 8).

To summarize, the present invention provides an antibacterial material RMG and a method of synthesizing and using the same. Since the antibacterial material utilized the reduced GO as a substrate and functionalized with the magnetic and aldehyde thereon, it is similar to the photocatalyst products which has low cyotoxicity. The antibacterial material provided in the present invention has potential for being photocatalyst and can be extensively applied to biomedical, health care or environmental cleaning. Furthermore, the antibacterial material can be attracted by a magnet to move or aggregate easily for further reusability.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. An antibacterial material RMG for capturing and effective photothermal killing of bacteria by formula I:

$$RMG \qquad \text{I}$$

wherein R is formaldehyde, straight chain C1-10 alkyl, branched C3-10 alkyl, C3-10 cycloalkyl, phenyl, phenylalkyl aldehyde straight chain alkyl di-aldehyde, branched alkyl di-aldehyde, aromatic di-aldehyde, alkylaromatic di-aldehyde, heteroaromatic di-aldehyde, alkyl heteroaromatic di-aldehyde or their mixture, M is a magnetic material, and G is reduced graphene oxide.

2. The antibacterial material according to claim 1, wherein the magnetic material is triiron tetroxide.

* * * * *